United States Patent
Mitchell et al.

(10) Patent No.: US 9,588,067 B2
(45) Date of Patent: Mar. 7, 2017

(54) EXAMINING POROUS SAMPLES

(75) Inventors: Jonathan Mitchell, Great Cambourne (GB); Edmund Fordham, Cambridge (GB)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 665 days.

(21) Appl. No.: 14/005,253

(22) PCT Filed: Mar. 8, 2012

(86) PCT No.: PCT/IB2012/051093
§ 371 (c)(1),
(2), (4) Date: Sep. 13, 2013

(87) PCT Pub. No.: WO2012/123863
PCT Pub. Date: Sep. 20, 2012

(65) Prior Publication Data
US 2013/0342208 A1   Dec. 26, 2013

(30) Foreign Application Priority Data
Mar. 14, 2011   (GB) .................................. 1104255.3

(51) Int. Cl.
*G01N 24/08* (2006.01)
(52) U.S. Cl.
CPC ................... *G01N 24/081* (2013.01)
(58) Field of Classification Search
CPC .................................................. G01N 24/081
See application file for complete search history.

(56) References Cited

U.S. PATENT DOCUMENTS 5,351,525 A   10/1994  Ragazzini et al.
5,886,525 A   3/1999   Yesinowski et al.
(Continued)

FOREIGN PATENT DOCUMENTS

WO   2007003218   1/2007
WO   2010003236   1/2010

OTHER PUBLICATIONS

Balcom et al., "Single-Point Ramped Imaging with T1 Enhancement (SPRITE)," Journal of Magnetic Resonance, Series A, 1996, vol. 123(1): pp. 131-134.
(Continued)

*Primary Examiner* — G. M. Hyder

(57) ABSTRACT

Apparatus for examining a fluid-containing porous sample, by a combination of centrifuging to move fluid into, out of, and/or within the sample and NMR to monitor the amount of fluid present at locations within the sample has a magnet system to provide a magnetic field; and a centrifuge rotor comprising a holder (18) for the sample and mounted to move the sample within the magnetic field. The apparatus preferably includes gradient coils (16, 116) superimposing a magnetic field gradient onto a field provided by magnets (11, 12, 111, 112). At least one radio-frequency coil (20) is located on the centrifuge rotor in a position 10 which surrounds the sample in the holder. The coil axis is transverse to the magnetic field and field gradient when measurement is made. Consequently NMR measurement of the distribution of fluid in the sample can be made while the centrifuge is in motion.

19 Claims, 2 Drawing Sheets

(56) References Cited

U.S. PATENT DOCUMENTS

| | | | |
|---|---|---|---|
| 6,415,649 B1 | 7/2002 | Spinler et al. | |
| 6,720,769 B2* | 4/2004 | Gerald, II | G01R 33/48 324/318 |
| 7,053,611 B2 | 5/2006 | Freedman | |
| 7,352,179 B2 | 4/2008 | Chen et al. | |
| 2006/0116828 A1* | 6/2006 | Chen | G01N 24/08 702/22 |
| 2010/0156414 A1* | 6/2010 | Sakellariou | G01R 33/307 324/309 |
| 2011/0050223 A1* | 3/2011 | Balcom | G01R 33/305 324/307 |
| 2012/0133358 A1* | 5/2012 | Broz | G01N 24/084 324/307 |
| 2013/0088232 A1* | 4/2013 | Inukai | G01N 24/08 324/321 |
| 2014/0055134 A1* | 2/2014 | Fordham | G01R 33/4818 324/309 |

OTHER PUBLICATIONS

Bloch, "Nuclear Induction," Physical Review, Oct. 1946, vol. 70(7 & 8): pp. 460-474.

Bloembergen et al., "Relaxation Effects in Nuclear Magnetic Resonance Absorption," Physical Review, Apr. 1948, vol. 73(7): pp. 679-712.

Brownstein et al., "Importance of classical diffusion in NMR studies of water in biological cells," Physical Review A, Jun. 1979, vol. 19(6): pp. 2446-2453.

Callaghan, "3.3: Reconstruction in two dimensions," Principles of Nuclear Magnetic Resonance Microscopy Clarendon: Oxford, 1991: pp. 121-129.

Cano Barrita et al., "OTC 19234: Capillary Pressure Measurement in Petroleum Reservoir Cores with MRI," Offshore Technology Conference, 2008: pp. 1-11.

Chen et al., "The Effect of Gravity Degradation on Low-Speed Centrifuge Capillary Pressure Data," AIChE Journal, Mar. 1995, vol. 41(3): pp. 469-480.

Chen et al., "Measurement of rock-core capillary pressure curves using a single-speed centrifuge and one-dimensional magnetic-resonance imaging," The Journal of Chemical Physics, 2005, vol. 122: p. 214720-1-214720-8.

Emid et al., "High Resolution NMR Imaging in Solids," Physica, 1985, vol. 128B: pp. 81-83.

Forbes, "Simple and Accurate Methods for Converting Centrifuge Data Into Drainage and Imbibition Capillary Pressure Curves," The Log Analyst, Jul.-Aug. 1994: pp. 31-53.

Fordham et al., "Imaging Multiexponential Relaxation in the (y, loge, T1) Plane, with Application to Clay Filtration in Rock Cores," Journal of Magnetic Resonance Series A, 1995, vol. 113: pp. 139-150.

Glover, "Chapter 8: Capillary Pressure," Formation Evaluation MSc Course Notes, 2001: pp. 84-94, <http://www2.ggl.ulaval.ca/personnel/paglover/CD%20Contents/Formation%20Evaluation%20English/Chapter%208.PDF>.

Green, "Capillary Pressure Curves Determined by Direct Measurement of the Saturation using Magnetic Resonance Imaging," Canadian Well Logging Society InSite, May 2009, vol. 28(1): pp. 20-25.

Haacke et al., "Chapter 9: One-Dimensional Fourier Imaging, k-Space and Gradient Echoes," Magnetic Resonance Imaging—Physical principles and sequence design, 1999: pp. 139-163.

Hassler et al., "Measurement of Capillary Pressures in Small Core Samples," Petrol. Trans., 1945, vol. 160: pp. 114-123.

Hürlimann, "Effective Gradients in Porous Media Due to Susceptibility Differences," Journal of Magnetic Resonance, 1998, vol. 131: pp. 232-240.

Kaffanke et al., "Application of the chirp z-transform to MRI data," Journal of Magnetic Resonance, 2006, vol. 178: pp. 121-128.

Li et al., "Quantitative discrimination of water and hydrocarbons in porous media by magnetization prepared centric-scan SPRITE," Journal of Magnetic Resonance, 2007, vol. 186: pp. 282-292.

Li et al., "Spin echo SPI methods for quantitative analysis of fluids in porous media," Journal of Magnetic Resonance, 2009, vol. 198: pp. 252-260.

Marica et al., "Spatially resolved measurement of rock core porosity," Journal of Magnetic Resonance, 2006: pp. 136-141.

Mastikhin et al., "Water Content Profiles with a 1D Centric SPRITE Acquisition," Journal of Magnetic Resonance, 2002, vol. 156: pp. 122-130.

Mitchell et al., "Spatially resolved nuclear magnetic resonance studies of planar samples," Progress in Nuclear Magnetic Resonance Spectroscopy, 2006, vol. 48: pp. 161-181.

Rioux et al., "Article 16: An Accurate Nonuniform Fourier Transform for SPRITE Magnetic Resonance Imaging Data," ACM Transactions on Mathematical Software, Aug. 2007, vol. 33(3): pp. 1-21.

Ruth et al., "Measurement and Interpretation of Centrifuge Capillary Pressure Curves—The SCA Survey Data," The Log Analyst, Sep.-Oct. 1995: pp. 21-33.

Canadian Examination Report for corresponding Canadian Application No. 2,830,021 dated Feb. 22, 2016, 5 pp.

* cited by examiner

EXAMINING POROUS SAMPLES

CROSS-REFERENCE TO RELATED APPLICATIONS

This application is a U. S. National Stage Application under 35 U.S.C. §371 and claims priority to Patent Cooperation Treaty Application Number PCT/IB2012/051093 filed Mar. 8, 2012, which claims priority to British Patent Application No. GB1104255.3 filed Mar. 14, 2011. Both of these applications are incorporated herein by reference in their entireties.

FIELD OF THE INVENTION

This invention is concerned with the examination of porous samples undergoing forced drainage or imbibition and thus concerns testing of materials. The invention is not limited to specific reasons for testing nor to samples of specific origin, but in some forms of the invention the porous samples may be rock cores collected as samples underground whilst drilling. The collection of such samples and their examination may be done in connection with exploration for, or exploitation of, hydrocarbons in underground reservoirs. It is also possible that it may be done in connection with exploration for, or utilisation or management of underground water, or in connection with schemes for the storage of captured carbon dioxide.

BACKGROUND OF THE INVENTION

It is conventional practice when drilling through underground rock to drill around a central cylinder of rock which is subsequently detached and brought to the surface as a sample, habitually referred to as a rock core. Once brought to the surface, rock cores may be subjected to various measurements and tests.

One known test procedure entails centrifuging the sample at various speeds and measuring the amount of liquid which drains from the sample at the various speeds. This enables determination of a capillary pressure curve as described in Hassler and Brunner "Measurement of Capillary Pressure in Small Core Samples", Trans. AIME, vol 160, pages 114-123 (1945) also published as Society of Petroleum Engineers paper SPE 945114-G. This method is also discussed in Chen and Balcom, Journal of Chemical Physics vol 122, 214720 (2005) and the related U.S. Pat. No. 7,352,179 (Chen and Balcom, Green Imaging Technologies). The teaching of Chen and Balcom develops the method further by proposing that the amount of fluid in the porous sample is determined by nuclear magnetic resonance (NMR). After centrifuging for a period of time, the sample is removed from the centrifuge and placed in a nuclear magnetic resonance spectrometer. A quantitative method for determining the spatial distribution of fluid used after transfer to the NMR spectrometer is the "SPRITE" technique described in Balcom et al "Single Point Ramped Imaging with $T_1$ Enhancement (SPRITE)", J. Magn. Reson. A vol 123, pages 131-134 (1996).

U.S. Pat. No. 7,352,179 envisages that the centrifuge and the NMR spectrometer may be separate pieces of apparatus. The sample will be transferred from the former to the latter after centrifuging for a period of time. The document recognizes that "Centrifugation creates a non-equilibrium fluid distribution which will change due to capillarity, diffusion and inlet/outlet drying once the sample is removed from the centrifuge". It is suggested that these changes may be measured by NMR after centrifugation.

FIG. 20 of U.S. Pat. No. 7,352,179 shows an alternative arrangement in which a disc shaped sample is centrifuged by spinning around the disc axis while located inside the radio frequency coil and magnetic field of an NMR spectrometer. The disc axis is transverse to the magnetic field direction, so that the disc spins in a plane parallel to the field direction. U.S. Pat. No. 7,352,179 states that the amount of fluid within the spinning rock disc can be monitored by "NMR bulk measurements, such as free induction decay and CPMG (Carr-Purcell-Meiboom-Gill)". After centrifuging for a period of time, the spin is ceased and a 2D magnetic resonance imaging method is used to obtain the 2D spatial distribution of fluid in the plane of the disc and from this to assess saturation radially relative to the disc axis.

SUMMARY OF THE INVENTION

The present invention centrifuges a porous sample in the magnetic field of apparatus for NMR measurements, but does so in a different arrangement to that proposed in FIG. 20 of U.S. Pat. No. 7,352,179. NMR measurements to determine fluid distribution in the sample can be carried out while the sample is being centrifuged.

In a first aspect, this invention provides apparatus for examining a fluid-containing porous sample, comprising:
  a magnet system to provide a magnetic field; and
  a centrifuge rotor comprising a holder for the sample and
    at least one radio-frequency coil positioned to surround the sample in the holder,
where the mounting of the rotor and the position of the sample holder and the radio-frequency coil(s) thereon are such that the sample and coil(s) travel within the magnetic field as the rotor turns, with the or each coil axis transverse to the magnetic field for causing and detecting nuclear magnetic resonance of nuclei in the fluid in the sample within the magnetic field.

In a second aspect, the invention provides a method for examining a fluid-containing porous sample comprising:
  placing the sample within at least one radio frequency coil,
  centrifuging the sample by rotating both the sample and the radio frequency coil or coils in a path which extends within a magnetic field with the axis of the or each coil transverse to the magnetic field, and
  using the radio frequency coil or coils around the sample to cause and to observe nuclear magnetic resonance of nuclei in the fluid in the sample while it is within the magnetic field.

The magnet system and the radio frequency coil(s) are the functional parts of a NMR spectrometer. NMR spectrometry is not dependent on movement of the sample and coil(s) within the magnet system. Hence, it can be envisaged within the scope of this invention that the centrifuge rotor and magnet system could all rotate together. This could be achieved using single-sided or "unilateral" magnets as reviewed by Mitchell et al "Spatially resolved nuclear magnetic resonance studies of planar samples", Prog. Nucl. Magn. Reson. Spect. vol 48, pages 161-181 (2006). However, it is likely to be more convenient that the main mass of the magnet system remains stationary so that the sample and coil(s) move within the magnetic field as the rotor turns. However, as will be illustrated below, even though the main mass of the magnet system is stationary some portion of the magnet system could be carried on the rotor so as to rotate with it.

One radio frequency coil (or possibly more than one coil) may be used for applying radio frequency energy to the sample while a second coil (or possibly more than one coil) may be used to pick up radio frequency energy from the sample. In this event the coil which is excited to apply energy and the second coil to receive energy may possibly be wound one on top of the other. Alternatively the same coil or coils may be used to apply energy to the sample and to receive energy from the sample, particularly if energy is applied as a pulse and energy from the sample is received subsequently to the pulse.

A further possibility is that multiple coils may be provided in order to bring about resonance of more than one nucleus. For instance, one or two coils could serve for excitation and detection of $^1$H NMR while a further coil or pair of coils could be used for $^{13}$C NMR.

Locating the radio frequency coil or coils around the sample on the centrifuge rotor has the advantage that the sample is in proximity to the coil(s). The apparatus can be designed such that the samples can fill a high proportion of the volume within the radio frequency coil(s). It also enables NMR measurements to be carried out while the centrifuge rotor is in motion and thus it is possible to make real-time observation of fluid within the porous sample as it is being centrifuged. This eliminates the possibility of redistribution of the fluid in the porous sample under gravity or capillary forces which might otherwise occur during the time taken to decelerate and stop the centrifuge and/or to transfer the sample from a centrifuge to a separate NMR spectrometer. Redistribution under gravity can be especially deleterious if the core is of high permeability; capillary forces will be especially problematic if fluid mobility (ratio of permeability to viscosity) is high or capillary pressure is large. Moreover, the whole process of making measurements on a sample can be quicker than with existing methods. It can also be envisioned that the process of acquiring NMR data from the sample as it is rotated at incrementally higher or lower speeds may be automated.

The main magnetic field could be provided by one or more electromagnets, but it may be more convenient that the magnet system includes at least one permanent magnet. A pair of permanent magnets mounted facing each other may be used to provide a magnetic field in a space between them. Another possibility is to use pole pieces which carry magnetic flux from a single permanent magnet or from an electromagnet.

In significant forms of this invention the magnet system provides a magnetic field with a field gradient arranged such that the strength of the magnetic field varies in a direction radial to the rotation axis. This variation in field strength leads to different resonant frequencies along one dimension of the sample and enables NMR measurements to observe the fluid distribution in one dimension within the sample. Locating the radio frequency coil or coils with the sample on the rotor in accordance with this invention has the advantage that this spatial distribution of fluid can be observed while the centrifuge is in motion. It is possible that additional field gradients may be provided so as to observe spatial distribution of fluid in two or even three dimensions.

A magnetic field gradient can be provided by shaping of the magnetic poles, for example by using a pair of magnets which vary in thickness of permanently magnetic material or in spacing between them or both of these, so as to produce a gradient in the strength of magnetic field between them.

Another possibility is that a magnetic field gradient may be provided by means of one or more gradient coils (usually a pair) which superimpose a field gradient onto a uniform magnetic field such as may be provided by permanent magnets. It is possible to provide a field gradient which is the same at all azimuthal directions of the centrifuge rotor and sample carried thereon by using a magnet system and gradient coils which are circularly symmetric around the rotational axis of the centrifuge rotor. Then, if the radio frequency coil or coils also extend radially relative to the axis of rotation, the centrifugal rotation will not be visible to the NMR measuring system.

Shaping of the magnetic poles will produce a magnetic field gradient which is fixed. Gradient coils can be operated to produce a "fixed magnetic field gradient but they can also be operated with variation of the current in the coils so as to produce a field gradient of varying magnitude. In particular gradient coils may be operated to vary the magnetic field in repeated pulses as required by some NMR techniques. Although the centrifugal rotation should not be visible to the NMR system, it may nevertheless be arranged that the NMR measurements are made at only one azimuthal position of the rotor, as a precaution against any slight lack of uniformity in the magnetic field or magnetic field gradient.

The NMR spectrometer must be provided with a power supply and electronic equipment to operate it. This may be the same as or similar to the power supplies and operating electronic systems used in conventional NMR spectrometers. The electronic system is expected to comprise means for generating radio frequency signals to excite the radio frequency coil (or at least one coil if there is more than one) and thereby apply energy to the sample. The electronic system is also expected to comprise means for receiving radio frequency signals. There may be means for processing received signals, possibly including analogue to digital conversion of the signals, and/or means for sending them to other equipment for processing. At least some processing of received signals may be carried out using a programmed computer, which may be integrated into the NMR spectrometer or may be a separate piece of equipment. It is typical for spatially resolved data, acquired in the time domain, to be Fourier Transformed at the processing stage to form a distribution of frequencies that is consistent with the one-dimensional projection of the fluid content of the sample (i.e. an image profile). Locating the coil or coils on the centrifuge rotor creates a question of how to communicate with the moving coil(s). One possibility is to transmit radio frequency signals across a contactless connection between stationary and moving conductors. At radio frequencies, such a contactless connection could be provided by conductors which come into close proximity or by means of inductively coupled coils. An alternative approach involves locating an electronic system for sending and receiving radio frequency signals and for processing or storing the observed data in a position such that this system will rotate with the centrifuge rotor. The electronic system is constructed to operate automatically while the centrifuge is turning and the data obtained is stored in memory from which it is downloaded after the centrifuge has stopped. The data may also be transmitted via a "wireless" radio device to a stationary radio receiver mounted inside the centrifuge drum but remote from the rotor. The radio receiver would then communicate the data to the NMR spectrometer or to a data storage device using a conventional cable.

Embodiments of the invention and further features which may be used will now be described with reference to the accompanying drawings. This description is exemplary in nature and is not intended to limit the scope of the invention. Except where clearly inappropriate or expressly noted, features and components of different embodiments may be employed separately or used in any combination.

DETAILED DESCRIPTION

Figure 1:
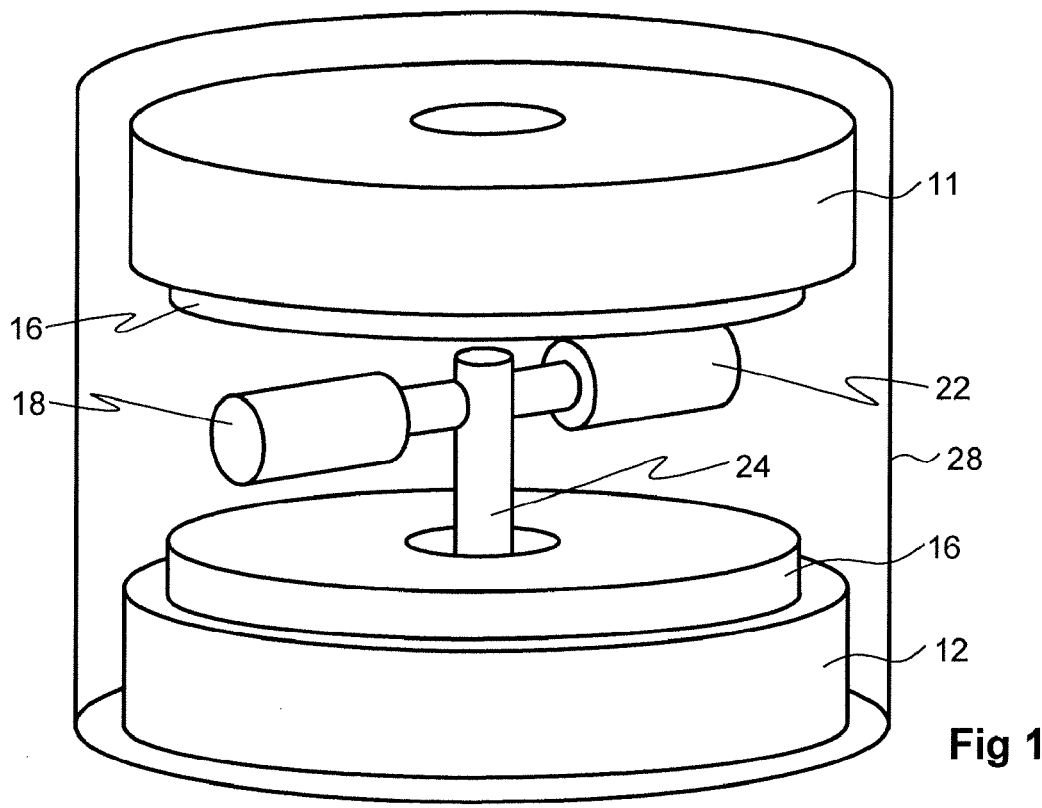
FIG. 1 is a schematic perspective view of combined centrifuge and NMR apparatus.
Figure 2:
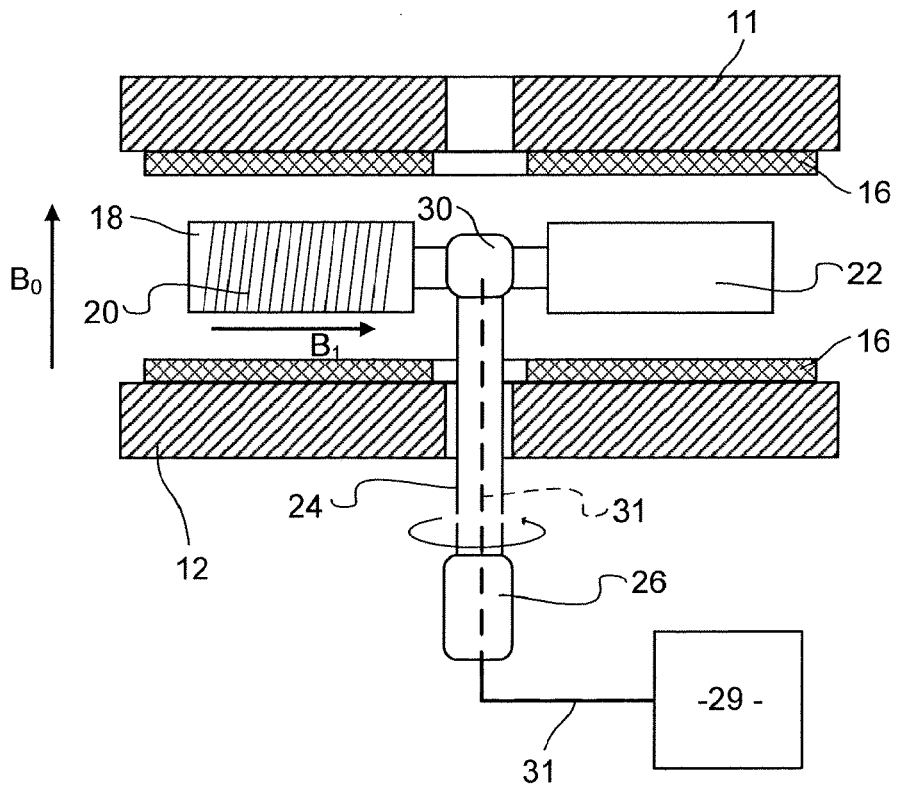
FIG. 2 is a cross sectional view of the apparatus of FIG. 1.

The apparatus shown in FIGS. 1 and 2 has a magnet system with circular symmetry. It has a pair of annular permanent magnets 11, 12 arranged one above the other on a common vertical axis facing each other but spaced apart so that a magnetic field extends in the vertical direction (which is here regarded as the z direction of Cartesian coordinates) as indicated by the arrow $B_0$ in FIG. 2. In this illustration each magnet has its S pole on top, so the magnetic field $B_0$ extends from a S pole piece provided by magnet 12 to a N pole piece provided by magnet 11. Both permanent magnets 11, 12 may be made of rare earth compounds to give a high magnetic field. Specifically, they may possibly be neodymium iron boron (NdFeB) magnets which can be manufactured in the required shapes or assembled from smaller blocks.

In order to create a field gradient, annular magnetic field gradient coils 16 are positioned adjacent the magnet poles 11, 12 and coaxial with them. These coils 16 have spiral windings in the same sense and the spacing between turns of the spiral is arranged to vary such that when the coils are energised the magnetic field has a gradient denoted as $G_r = \delta B_0 / \delta r$ extending radially from the axis to the periphery of the magnetic field. This field gradient is proportional to the current in the coils 16 and its magnitude can thus be controlled.

The permanent magnets 11, 12 should desirably provide a uniform magnetic field in the space between them. The gradient coils 16 are desirably wound such that the field gradient superimposed on the magnetic field of the permanent magnets is uniform across most of the distance between the inner and outer radii of the annular magnets 11, 12. The upper magnet 11 is shown as having the same shape as the lower magnet 12, but it is possible that the upper magnet 11 could be a disc rather than an annulus.

It may be noted that a magnet system which has circular symmetry is unusual in magnetic resonance apparatus. Gradient coils are more usually designed to provide uniform field gradients in each of the Cartesian axis directions (x, y, z).

A centrifuge rotor is located in the space between the coils 16. It is mounted to rotate horizontally around the vertical axis of the magnet system. The centrifuge rotor comprises a holder 18 for a fluid-impregnated sample and a counterweight 22, both attached to a central drive shaft 24 which extends through the central aperture of magnet 12 and is turned by a drive motor 26. The sample holder 18 is surrounded by a radio frequency coil 20 which generates a radio frequency field $B_1$ when excited with a radio frequency current. The magnets 11, 12, the gradient coils 16 and the centrifuge rotor are all contained within a casing 28 of the centrifuge. Electronic systems for providing radio frequency signals to the coil 20 and receiving radio frequency signals from it are indicated at 29.

Because of the circular symmetry of both permanent magnet and gradient coils, the magnetic field and the magnetic field gradient are uniform with respect to azimuth around the axis of the magnet system and therefore unchanging with position of the centrifuge rotor even whilst the centrifuge is rotating.

Because the radio frequency coil 20 has an axis perpendicular (at all azimuths during its rotation) to the static magnetic field in the space between the coils 16, the radio frequency field $B_1$ is orthogonal to the static field $B_0$, for all azimuthal positions of the rotor. Hence, NMR measurements can be made whilst the centrifuge is in operation, regardless of the rotor position. Moreover, because there is a radial field gradient, the NMR measurements can determine the radial position at which resonance occurs as well as the magnitude of resonance at that position and thus determine a distribution of fluid along the length of the sample in the holder 18. It will be appreciated that it is conventional practice in NMR apparatus to orient a radio-frequency coil so that its field $B_1$ is orthogonal to field $B_0$. Magnetic resonance is possible if the fields $B_1$ is obliquely transverse to field $B_0$ but such an arrangement is less efficient. It is convenient, in the arrangement shown here, that the radio frequency coil 20 is wound as a solenoid such that the field $B_1$ is orthogonal to both the static field $B_0$ and direction of rotation. However, other radio frequency coil designs, such as a saddle coil or birdcage coil, could be used whereby the field $B_1$ would still be orthogonal to the static field $B_0$ but parallel to the direction of rotation.

The radio frequency input and output signals to and from the coil 20 are carried by stationary coaxial cables 31 extending inside the drive shaft 24 which is hollow. Within a box 30 at the head of shaft 24 there is a contactless radio frequency coupling to connections to the coil 20. This contactless radio frequency coupling may be achieved by bringing the fixed and moving conductors into close proximity with only a small air gap between them. Another possibility is to use a pair of inductive coupling loops, one rotating, the other fixed, so as to form a simple radio frequency transformer.

It is possible that some or all of the electronic circuitry for the radio frequency signals, such as a first stage radio frequency pre-amplifier, or such an amplifier together with an analogue to digital converter, could be located on the rotor, perhaps within the volume of the counter weight 22 so that an amplified analogue radio frequency signal or a digital signal was passed through the contactless coupling.

It will be recognized that the arrangement shown involves electrically conductive parts moving in a magnetic field. However, because the magnet system creates a circularly symmetric magnetic field, the conductive parts will experience a constant rather than changing magnetic field and unwanted induction of current will be small. Moreover, any induced signals are likely to be at the frequency of the centrifuge rotor speed and so at frequencies which are easily removed by filtering because they are much lower than the frequencies of the radio frequency signals used in NMR measurements.

One possible variation of the arrangement described above has a second sample holder and radio frequency coil in place of the counterweight 22, allowing concurrent investigation of two samples. It is also possible that the rotor could have additional arms carrying further sample holders and associated coils, so that the number of concurrent samples is even higher. Simultaneous NMR measurements on multiple samples is possible with present-day multi-channel NMR spectrometers.

In order to enable access to the sample holder (or holders) 18 a mechanical arrangement may be provided for moving the magnets 11, 12 apart. This could, for instance, be a mechanism such as screw jacks for lifting the upper magnet 11. Another possibility would be to lift the entire magnet arrangement 11 and 12 and the rotor system by mechanical means, where the rotor shaft 24 becomes detached from the drive motor 26. In this implementation the cable 31 may be retractable to facilitate vertical movement of the rotor.

Alternatively, a small gap could be engineered in the upper magnet 11 and upper gradient coil 16 so that the sample could be accessed without moving the magnet pole(s). By shaping of the pole pieces it is envisioned that the static field $B_0$ and magnetic field gradient would still be uniform to a sufficient degree at all azimuths, although NMR measurements would likely be conducted when the sample is not adjacent to this access gap.

A further possibility for access to the sample holder would be to provide an access door in the centrifuge drum, although such a door in an armoured drum would need to be of heavy construction in order to adhere to safety requirements.

Figure 3:
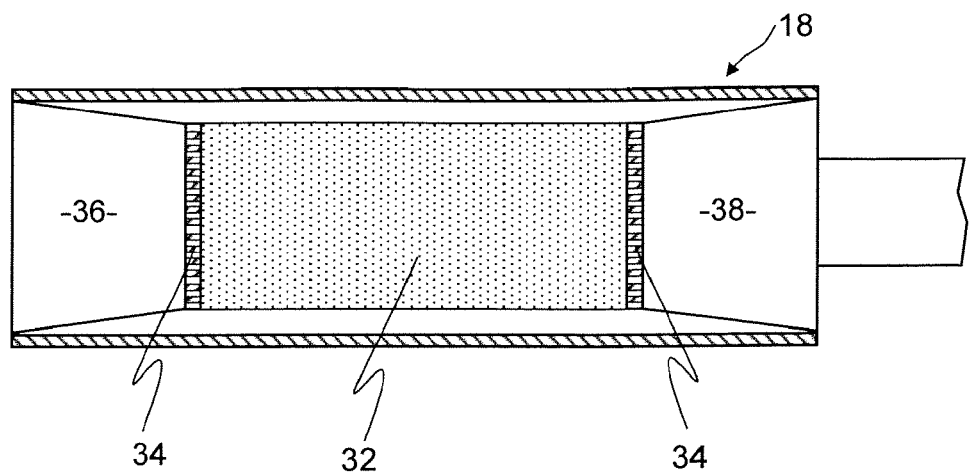
FIG. 3 is a schematic longitudinal cross section of a sample holder to be used with the apparatus of FIGS. 1 and 2.

FIG. 3 shows schematically the positioning of a rock core 32 within sample holder 18. The cylindrical sample has a fluid-impermeable sleeve wrapped around its outer cylindrical surface and is confined between plates 34 at each end. These plates 34 have multiple perforations to allow fluid to flow axially into or out of the sample. A drain reservoir 36 for fluid centrifuged out of the sample is provided at the radially outer end, and a reservoir 38 for fluid to be imbibed by the core 32 is provided at the opposite end. Thus the apparatus can be used in imbibition experiments in which the centrifuge urges fluid into the core as well as experiments in which centrifuging causes fluid to drain from it. Displacement experiments in which one fluid enters the core while another is expelled from it can also be conducted.

The materials used in construction of the sample holder 18 should be transparent to magnetic fields and radio frequency electromagnetic radiation. Since the NMR measurement is a measurement of $^1H$ nuclei in most implementations of this invention, it is also desirable that the rotor should be constructed using materials with a low content of hydrogen atoms, or materials in which $^1H$ nuclei have such short relaxation times that their NMR signal does not matter. Possible materials include the hard polymers PEEK (poly(ether-ether-ketone)) and or TORLON (a poly(amide-imide)) or composite materials based on them. A further possibility is an inorganic ceramic material such as zirconia.

Using a core holder as shown in FIG. 3, it is possible to carry out experiments in which liquid is centrifuged out of a core, experiments in which liquid is centrifuged into a core and experiments in which one fluid replaces another, for example experiments in which oil (containing $^1H$ nuclei detectable by NMR) is replaced with $D_2O$ which is not observed by $^1H$ NMR. It is also feasible to carry out experiments in which both fluids contain detectable nuclei (for example when $H_2O$ displaces oil) by detecting resonance signals from both fluids simultaneously and then separating the signals in a post-acquisition processing stage. Such post acquisition processing may use techniques for distinguishing materials by means of contrast in NMR parameters such as $T_1$ or $T_2$ relaxation or diffusion coefficient D. It is envisaged that the fluid(s) centrifuged out of or into the core will be liquids, which may be hydrophobic or hydrophilic in nature. However, it is also possible that experiments may be carried out in which a fluid centrifuged out of or into the core is a gas. This may be a gas which is detectable by NMR such as $SF_6$ in which $^{19}F$ is capable of magnetic resonance.

Using a single apparatus to provide both centrifuge and NMR functions facilitates experiments under conditions which are not ambient at the earth's surface (whereas maintaining the same non-ambient conditions in two separate pieces of apparatus and during transfer of the sample from one to the other is inconvenient). It is already conventional to heat permanent NMR magnets to a controlled temperature above ambient, as part of a procedure for maintaining constant temperature and hence field stability. Such a heating and temperature control arrangement may be extended to the whole of the apparatus shown in FIGS. 1 and 2. The apparatus may then be used for conducting experiments in which the sample is maintained at a temperature above ambient which is better representative of conditions in a subterranean reservoir. It would also be possible to carry out experiments at an elevated pressure, either by pressurizing the interior of the sample holder 18 before placing it on the rotor, or by using a pressure vessel as the outer casing. A further possibility would be to carry out experiments in which the temperature or pressure was maintained below ambient: a temperature below ambient could in particular be used for experiments on gas hydrates.

Figure 4:
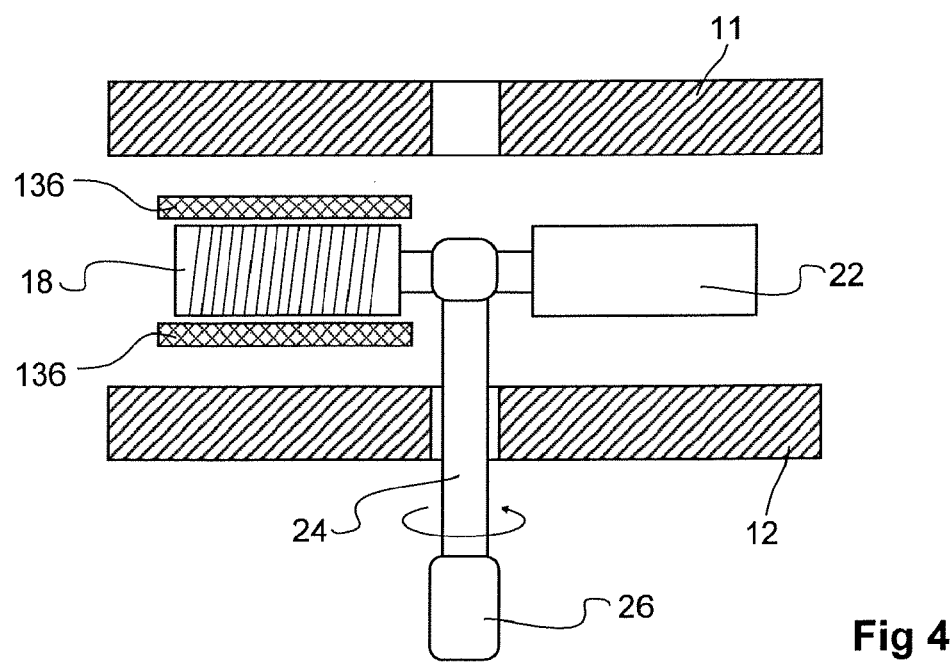
FIG. 4 is a schematic cross-sectional view of a second form of combined centrifuge and NMR apparatus.

FIG. 4 shows a possible alternative arrangement of apparatus. Instead of using fixed circular gradient coils 16 in a circularly symmetric magnet system, two gradient coils 136 are carried on the centrifuge rotor, above and below the sample holder 18. These coils 136 are wound such as to create a gradient magnetic field in the radial direction, along the length of the sample 18, so that the gradient coils 136 superimpose a field gradient on the uniform magnetic field created by the magnets 11 and 12. Because the field between the magnets 11, 12 is uniform and the gradient coils 136 are carried on the centrifuge rotor, the magnetic field and field gradient are constant, relative to the sample 18. By this arrangement the magnetic field and field gradient are the same for all measurements and the direction of the field induced by the radio frequency coil 20 is orthogonal to the static field, just as with the arrangement of FIGS. 1 and 2. It would also be possible to mount permanent magnets (smaller than magnets 11, 12) on the rotor to provide or contribute to a field gradient.

The apparatus shown in FIGS. 1 and 2 and also the apparatus shown in FIG. 4 provides a magnetic field gradient along the length of the core at the time of measurement. Consequently the magnetic field varies along the length of the core and this makes it possible to determine the distribution of fluid (specifically the amount of $^1H$ nuclei in the fluid) at every position along the length of the core, because the resonant frequency of the spins in the nuclei is dependent on position within the magnetic field gradient.

As discussed in textbooks on Magnetic resonance Imaging, there are a considerable number of imaging techniques for using NMR to determine the spatial distribution of nuclei which display magnetic resonance. The present invention is not limited to any specific imaging protocol.

One magnetic resonance imaging technique which may be used in this invention is the Single Point Ramped Imaging with $T_1$ Enhancement "SPRITE" technique mentioned earlier in which radio frequency energy is supplied as a broadband pulse and the echo of emitted energy is determined with a magnetic field gradient which is ramped in multiple steps. This technique is described (as already mentioned) by Balcom et al in J. Magn. Reson. Series A vol 123, pages 131-134 (1996). It has the advantage that it can acquire quantitative data for a complete magnetic resonance image of the core rapidly.

One issue which arises when using this technique in the present context is that as fluid is caused to move within the rock core the longitudinal relaxation time $T_1$ will also change as the amount of filled or partially filled porosity changes. Quantification of the signal amplitude can be improved by employing a so-called 'centric-scan' or 'double-half k-space profiling' protocol as taught by Mastikhin et al in "Water content profiles with a 1D centric SPRITE acquisition" J. Magn. Reson Vol 15 pages 122-130 (2002). An algorithm for use in summing profiles obtained from the set of points as each measurement is made has been disclosed by Kaffanke et al "Application of the chirp z-transform to MRI data" J. Magn. Reson. vol 178 pages 121-128 (2006) and by Rioux et al "An accurate nonuniform Fourier transform for SPRITE magnetic resonance imaging data" ACM Trans. Math. Software. vol 33 issue 3 pages 1-21 (2007). Alternatively, the $T_1$ relaxation time can be determined as a function of position using a appropriate encoding method; one such method is taught by Fordham et al "Imaging multiexponential relaxation in the (y, $\log_e T_1$) plane, with application to clay filtration in rock cores", J. Magn. Reson. Ser. A vol 113, pages 139-150 (1995).

Distinguishing materials by means of contrast in NMR parameters such as $T_1$ or $T_2$ relaxation or diffusion coefficient D is discussed for example in Li et al "Quantitative discrimination of water and hydrocarbons in porous media by magnetization-prepared centric-scan SPRITE" J. Magn. Reson. Vol 186 pages 282-292 (2007) and also (using contrast in $T_2$) in WO 2010/003236. The single-point class of imaging protocols (including SPRITE) are referred to as "phase" encoding methods. Spatially resolved NMR data can also be acquired using "frequency" encoding spin echo methods as described in Magnetic Resonance Imaging (MRI) text books, for example Chapter 9 of Haacke et al "Magnetic Resonance Imaging: Physical principles and sequence design" John Wiley & Sons, Inc. (1999). Contrast in NMR parameters such as $T_1$, $T_2$, and D can be incorporated readily in "frequency" encoded images. Techniques for this include magnetization preparation.

Conventional centrifuge experiments on rock cores impregnated with fluid (oil or water) entail centrifuging at various speeds for long enough to reach equilibrium at each speed and then the amount of fluid which has been driven out of the core at each speed is measured. The apparatus embodying this invention, as described here, can be used to carry out such experiments with the improvement that the amount of fluid at individual positions along the length of the core can be determined initially and determined while centrifuging. The centripetal acceleration will be different at different points along the length of the core and so determining fluid distribution along the length of the core can take the place of centrifuging at a number of speeds in succession.

The invention claimed is:

1. Apparatus for examining a fluid-containing porous sample, comprising:
   a magnet system to provide a magnetic field; and
   a centrifuge rotor comprising a holder for the sample and at least one radio-frequency coil positioned to surround the sample in the holder,
   where the mounting of the rotor and position of the sample holder and the radio-frequency coil(s) thereon are such that the sample and coil(s) travel within the magnetic field as the rotor turns, with coil axis transverse to the magnetic field for causing and detecting nuclear magnetic resonance of nuclei in the fluid in the sample within the magnetic field.

2. Apparatus according to claim 1 wherein the magnet system comprises a pair of magnet poles which are stationary and spaced apart and the rotor turns in the magnetic field between them.

3. Apparatus according to claim 1 wherein the magnet system provides a gradient in the magnetic field and the mounting of the rotor and position of the sample holder thereon are such that the strength of the magnetic field varies along a length of the sample.

4. Apparatus according to claim 3 wherein the magnet system comprises gradient coils which create the gradient in the magnetic field.

5. Apparatus according to claim 4 wherein the magnet system and the magnetic field are circularly symmetric around the rotational axis of the centrifuge rotor and the gradient coils create a magnetic field gradient extending radially relative to the rotational axis of the centrifuge rotor.

6. Apparatus according to claim 1 wherein the magnet system and the magnetic field are circularly symmetric around the rotational axis of the centrifuge rotor.

7. Apparatus according to claim 1 configured such that radio-frequency signals to and from the coil(s) on the centrifuge rotor are connected through contact-less connections.

8. Apparatus according to claim 1 wherein the sample holder is configured to hold a cylindrical sample with its axis orthogonal to the rotational axis of the centrifuge rotor.

9. Apparatus according to claim 8 wherein the sample holder is configured to hold the cylindrical sample between a pair of reservoirs for fluid.

10. Apparatus according to claim 1 having means to maintain the sample at a controlled temperature other than ambient temperature or at a controlled pressure other than ambient pressure.

11. Apparatus according to claim 1 wherein:
    the magnet system comprises a pair of magnet poles which are stationary and spaced apart and the rotor turns in the magnetic field between them;
    the magnet system and the magnetic field are circularly symmetric around the rotational axis of the centrifuge rotor; and
    the magnet system comprises gradient coils which create a magnetic field gradient extending radially relative to the rotational axis of the centrifuge rotor.

12. Apparatus according to claim 11 wherein the sample holder is configured to hold a cylindrical sample with its axis orthogonal to the rotational axis of the centrifuge rotor.

13. Apparatus according to claim 12 wherein the sample holder is configured to hold the cylindrical sample between a pair of reservoirs for fluid.

14. A method for examining a fluid-containing porous sample comprising:
    placing the sample within at least one radio frequency coil,
    centrifuging the sample by rotating both the sample and the radio frequency coil or coils in a path which extends within a magnetic field with the axis of the or each coil transverse to the magnetic field, and
    using the radio frequency coil or coils around the sample to cause and to observe nuclear magnetic resonance of nuclei in the fluid in the sample while it is within the magnetic field.

15. A method according to claim 14 wherein centrifuging the sample causes one fluid to drain from the sample and a second fluid to enter it.

16. A method according to claim 14 wherein the sample is a cylindrical rock core.

17. A method according to claim 14 wherein nuclear magnetic resonance is measured by applying a pulse of radio frequency energy and then receiving energy emitted from the sample.

18. A method according to claim 14 wherein centrifuging and nuclear magnetic resonance measurement are carried out at a controlled temperature other than ambient temperature or at a controlled pressure other than ambient pressure.

19. A method according to claim 14 wherein nuclear magnetic resonance data is acquired in such a way as to provide a spatial distribution of the fluid in the sample.

\* \* \* \* \*